United States Patent [19]
Lohrmann et al.

[11] Patent Number: 5,654,452
[45] Date of Patent: Aug. 5, 1997

[54] LIPOPHILIC CONTRAST AGENTS FOR USE IN HEPATOCYTE-SELECTIVE OIL-IN-WATER EMULSIONS

[75] Inventors: Rolf Lohrmann, La Jolla; Dung K. Hong, San Diego, both of Calif.

[73] Assignee: Molecular Biosystems, Inc., San Diego, Calif.

[21] Appl. No.: 477,388

[22] Filed: Jun. 7, 1995

[51] Int. Cl.$^6$ .................................................. G07C 233/00
[52] U.S. Cl. ........................ 554/37; 554/51; 554/55; 554/56; 554/61; 554/62; 554/63; 554/67; 554/103; 554/104; 554/107; 554/121; 554/123; 554/225; 554/226; 554/220; 554/218; 554/213; 560/8; 560/19; 560/37; 560/38; 560/47; 560/103; 560/105; 560/110
[58] Field of Search .................................. 424/450, 455; 252/310, 358; 560/8, 19, 37, 38, 47, 103, 105, 110, 226; 554/56, 55, 51, 37, 61, 62, 63, 67, 103, 104, 107, 121, 123, 225, 229, 226, 220, 213, 218

[56] References Cited

U.S. PATENT DOCUMENTS

| | | | |
|---|---|---|---|
| 4,873,075 | 10/1989 | Caunsell et al. | 424/1.1 |
| 5,401,483 | 3/1995 | Lohrmann et al. | 424/9 |

FOREIGN PATENT DOCUMENTS

WO94/02106 2/1994 WIPO.

Primary Examiner—Deborah D. Carr
Attorney, Agent, or Firm—Fish & Richardson P.C.

[57] ABSTRACT

Aromatic acid-derived lipophilic polyhalogenated compounds are provided for use as contrast agents in diagnostic imaging or as therapeutic agents. These compounds are particularly useful when incorporated into an oil-in-water emulsion for tissue-specific delivery to the liver. For hepatocyte-selective delivery, the emulsion is chylomicron remnant-like by being in a size range of 50 to 200 nm and having a composition simulating naturally-occuring chylomicron remnants.

41 Claims, 4 Drawing Sheets

Ia R=H
Ib R=Oleoyl

IIa R=H
IIb R=Oleoyl

IIIa R=H
IIIb R=Oleoyl

Oleoyl= CH$_3$(CH$_2$)$_7$CH= CH(CH$_2$)$_7$CO

Ia R=H
Ib R=Oleoyl

IIa R=H
IIb R=Oleoyl

IIIa R=H
IIIb R=Oleoyl

Oleoyl= $CH_3(CH_2)_7CH=CH(CH_2)_7CO$

LIPOPHILIC CONTRAST AGENTS FOR USE IN HEPATOCYTE-SELECTIVE OIL-IN-WATER EMULSIONS

BACKGROUND OF THE INVENTION

This application relates generally to polyhalogenated compounds for use in contrast imaging, and more particularly to an oil-in-water emulsion containing such compounds for use as a tissue-specific contrast agent and/or delivery vehicle for therapeutic agents incorporated therein.

Imaging agents are used for diagnostic modalities, such as computed tomography (CT), magnetic resonance (MR), ultrasound or nuclear medicine, to enhance the image contrast between tissue types. It is a shortcoming in the present state of the art that most of the currently used imaging agents are limited in action to the vascular and/or extracellular compartments. Thus, every tissue that receives a normal blood supply will also receive the diagnostic agent. Tissue-specific image enhancement is therefore compromised. Non-specific agents that reside in the extracellular space are useful primarily to discriminate anatomical features of tissues and structures. However, an imaging agent that can deliver a diagnostic agent to the intracellular environment of a targeted tissue could provide a means of assessing the metabolic and/or biochemical activity of the targeted tissue in addition to providing the standard anatomical visualization achieved with extracellular imaging agents.

In addition to the foregoing, agents that localize in the extracellular spaces are cleared very rapidly from the body. Due to the limitations of imaging hardware, the minimum period of time required to collect the data used to form a diagnostic image is predetermined. Consequently, a contrast agent that clears too quickly from the body must be administered in a very large dose in order to maintain a concentration gradient sufficient to achieve an acceptable quality of the image. Thus, use of many currently available diagnostic imaging agents is a complicated process balancing the benefits of image enhancement against the dangers of injecting large volumes of material into a living being in a short period of time. In the case of CT imaging, diagnostic imaging agents are commonly administered to the patient in volumes as large as 150 to 250 ml at rates of 1.5 to 2.5 ml/sec. Injection of currently available agents at this rate can induce nausea, headaches convulsions and other undesirable and dangerous side effects. There is thus a need for a tissue-specific delivery vehicle that concentrates the imaging agent in a single targeted organ or tissue type and thus permits slower, controlled injection of a substantially smaller dose. Of course, a lower dose would also minimize the; potential for toxicity and side effects, as well as preclude the need for expensive: power injectors.

For therapeutic purposes, such as the delivery of radioactive therapeutic agents, would be advantageous to target specific tissue and reduce the destructive effects of the radioactive agents on surrounding tissue.

Some known strategies for achieving tissue-specific delivery include the use of vehicles such as liposomes, antibody-linked conjugates, and carbohydrate derivatives of the targeting compound. However, many of these known vehicles cannot form acceptable complexes with the moiety to be delivered, or fail to accumulate the complexed moiety in the target tissue in quantities sufficient to be effective for imaging and/or therapy.

One of the most accurate, non-invasive radiologic examination techniques available for detection of hepatic masses is CT using water soluble, urographic contrast agents. However, the contrast agents commonly used in this well-known technique suffer from the typical limitations that plague other known contrast agents, including, for example, the requirement that large doses be administered, a nonspecific biodistribution, and an extremely short (<2 min) residence time in the liver. As a result, CT has not been consistently successful at detecting lesions smaller than about 2 cm in diameter. These significant limitations of the known agents preclude early detection and therapy of cancer, since many metastases are smaller than the detection limits of this CT technique.

The inability of water-soluble urographic agents to detect lesions less than 2 cm in diameter with acceptable consistency may be due, in part, to the rapid diffusion of these agents out of the vasculature into interstitial spaces, resulting in a rapid loss of contrast differential between normal liver tissue and tumors. There is, therefore, a need for a diagnostic contrast agent, or vehicle therefor, that delivers the contrast agent to the intracellular space of specific targeted tissue, such as liver tissue, so as to enhance the degree of selective visualization and further improve the detection limits of CT. A number of alternatives to water-soluble contrast agents have been investigated as potential liver CT contrast agents including, for example, radiopaque liposomes, iodinated starch particles, perfluoroctylbromide, iodipamide ethyl esters, and ethiodized oil emulsion (EOE-13). All of these agents are particulate in nature and of such a size that liver specificity is mediated primarily via sequestration by the reticulendothelial system (RES).

Liposomes, which are artificially prepared lipid vesicles formed by single or multiple lipid bilayers enclosing aqueous compartments, are particulate in nature, and hence, have potential for delivering agents contained therein to the RES. Investigators have attempted to load liposomes with both ionic and non-ionic water-soluble urographic or hepatobiliary contrast agents, or to incorporate brominated phosphatidylcholine into the bilayer membrane of the liposomes. However, stabilization of the resulting liposome against loss of contrast media from the bilayers has proven to be a major problem. Moreover, incorporation of neutral lipophilic agents into the bilayer is limited by the low solubility of the lipophilic agents in the membrane matrix and the restricted loading capacity of the liposome.

Several monobrominated perfluorocarbons have been evaluated as contrast agents in animals. The most common of these, perfluoroctylbromide, has been shown to concentrate in the reticuloendothelial cells of the liver, spleen, and other organs. The long residency times (weeks to months) and the large doses (5–10 g/kg) necessary for suitable opacification will most likely preclude the use of monobrominated perfluorocarbons in humans for diagnostic imaging purposes, unless a means of specifically delivering small doses to a targeted organ is developed.

The most promising of the investigational agents mentioned above, EOE-13, has been extensively studied in both animals and humans in the United States. EOE-13, an emulsion of iodinated poppy seed oil (37% iodine by weight) in saline, offered considerable improvement in the detection of space-occupying lesions in the liver and spleen as compared to conventional water-soluble urographic agents. Despite acceptable clinical diagnostic efficacy, a high incidence of adverse reactions, including fever, chills, thrombocytopenia, hypotension, and respiratory distress, was reported. Moreover, additional problems were encountered in the sterilization of the EOE-13 preparation. These problems led to discontinuation of the use of EOE-13 in humans.

Recently, investigators have demonstrated a direct relationship between the size of emulsion particles and involvement of macrophages. In this study, the investigators tested three iodinated lipid emulsions, including EOE-13, having mean particle diameters ranging from 400–2000 nm. They observed a marked swelling of Kupffer cells which, when coupled with sinusoidal endothelial damage, resulted in sinusoidal congestion. Sinusoidal congestion often activates macrophages, resulting in the release of toxic mediators which may be responsible, in part, for the adverse reactions seen with these relatively large-sized particulate, preparations. As a result, the investigators emulsified iodinated ethyl esters of fatty acids derived from poppyseed oil (Lipiodol™-UF, Laboratoire Guerbet, France) with egg yolk phospholipids, in order to provide a preparation of smaller, more uniform particle size, called Intraiodol (not commercially available; see, for example, Acta Radiologica, Vol. 30, pages 407–412 and 449–457, 1989).. Intraiodol™ emulsion has a particle size range of 100 to 650 nm (distribution means diameter 310 nm). Initial results obtained with Intraiodol in animals and humans demonstrated a significant reduction in adverse reactions relative to those observed with EOE-13. However, Intraiodol™ emulsion continues to suffer from many disadvantages common to other prior art iodinated lipid emulsion contrast agents, including failure to achieve true specificity due to inter alia, size and contamination of the liposome composition with foreign particulates, resulting in two disadvantages: 1) delivery to the RES, and 2) inability to achieve shelf and heat stability. Moreover, in this prior art compound, the iodine necessary for CT opacification is attached in an aliphatic linkage, which is well known to exhibit diminished in vivo stability.

Although Intraiodol™ emulsion, and other similar oil-in-water emulsions, have been called "chylomicron remnant-like" and "hepatocyte specific," these agents located significantly in the spleen, which does not contain hepatocytes. More particularly, a true hepatocyte-specific contrast agent will not locate substantially in the spleen, which does not contain hepatocytes. A true hepatocyte-specific contrast agent will not locate substantially in the spleen and other RES associated organs, unless there is saturation of the initial receptor-mediated process, so that there is a shift in delivery to the cells of the RES. Further, a true hepatocyte-specific agent is cleared primarily through the biliary system. None of the aforementioned emulsions has demonstrated these characteristics of hepatocyte-specificity in biliary clearance studies.

To summarize briefly the natural lipid transport system, lipids are transported in the plasma mainly in the form of free fatty acids, triglycerides, and cholesteryl esters. Free fatty acids are transported as a complex with plasma albumin, whereas triglycerides and cholesteryl esters are transported in the lipophilic core of plasma lipoprotein. The surface of a plasma lipoprotein membrane comprises a monolayer of phospholipid, cholesterol, and specific proteins known as apolipoproteins which regulate the entry and exit of particular lipids at specific targets. Cholesterol and triglycerides from dietary sources are absorbed by the intestinal tract and incorporated into chylomicrons, which are subsequently secreted into and transported through the thoracic duct until they reach the circulation. Once in circulation, there is a rapid transfer of apoprotein C-II from circulating high density lipoprotein to the chylomicrons. Once associated with apoprotein C-II, the chylomicrons are acted upon by lipoprotein lipase in the capillary beds of several peripheral tissues including adipose, muscle (skeletal and heart), and lung. Lipoprotein lipase hydrolyzes much of the core triglyceride to glycerol and free fatty acids, most of which are taken up by the tissues for storage or oxidation. The remaining triglyceride-depleted chylomicrons, called chylomicron remnants, now contain lesser amounts of triglycerides, with cholesteryl esters as the main lipid component and apoprotein B (Apo B) and apoprotein E (Apo E) as the major apoprotein components. Chylomicron remnants are cleared very rapidly from the circulation by the liver via a receptor-mediated process that recognizes Apo B and Apo E. While lipoprotein lipase is the enzyme responsible for the hydrolysis of plasma triglycerides in extrahepatic tissues, hepatic triglyceride lipase is implicated in hepatic triglyceride hydrolysis and remnant uptake by hepatocytes. Hepatic clearance of chylomicron remnants from the circulation occurs mainly via the hepatocytes (parenchymal cells) rather than Kupffer cells (nonparenchymal cells).

Radiopaque lipids are generally incorporated into such emulsions to create radiopaque embodiments of such contrast-producing oil-in-water emulsions. In iodinated embodiments, iodine-containing lipids known in the art include iodinated fatty acids in the form of glycerol or alkyl esters. However, the iodine-containing lipids are preferably synthetic aromatic compounds of known purity that are stabilized against in vivo degradation of the iodine linkage. Illustrative examples of radioactive or non-radioactive halogenated triglycerides useful in the practice of the invention include, without limitation, iodinated triglycerides of the type described in U.S. Pat. No. 4,73,075 issued on Oct. 10, 1989; U.S. Pat. No. 4,957,719 issued on Sept. 18, 1990; and U.S. Pat. No. 5,093,043 issued on Mar. 3, 1992. Exemplary iodinated triglycerides are 2-oleoylglycerol-1,3-bis[7-(3-amino-2,4,6-triodophenyl)heptanoate] (DHOG) and 2-oleoylglycerol-1,3-bis[4-(3-amino-2,4,6-triiodophenyl)butanoate] (DBOG).

However, these compounds are complicated and, hence, expensive to manufacture. Moreover, because such compounds generally require an oil carrier, it is difficult to sufficiently concentrate the radiopaque substance to accomplish certain diagnostic and/or therapeutic ends requiring a high concentration of the; radioisotope.

Accordingly, there remains a great need in the art for target-specific delivery vehicles or compositions, including contrast-producing oils and oil-in-water emulsions, for delivery of diagnostic, therapeutic, and other biologically active or inactive agents, particularly for hepatocyte specific contrast-producing oils and oil-in-water emulsions for delivery of diagnostic or therapeutic agents, such as radioisotopes, to the liver. There also remains a need in the art for low cost low molecular weight radiopaque contrast agents that are lipophilic in character for inclusion in such oil-in-water emulsions for delivery to target specific sites.

It is, therefore, an object of this invention to provide an improved oily or lipophilic radiopaque contrast agent that is inexpensive to manufacture and can be used in an oil-in-water emulsion or without an oil carrier as a target-specific delivery vehicle:, such as an hepatocyte selective delivery vehicle.

It is a further object of this invention to provide a delivery vehicle, specifically a target-selective oil-in-water emulsion for delivery of lipophilic agents, or lipophilic derivatives of water soluble agents, such as contrast agents, to the intracellular spaces of the targeted tissue.

It is another object of this invention to provide a target-specific delivery vehicle, specifically a hepatocyte-selective oil-in-water emulsion, which is chylomicron remnant-like with respect to size and biodistribution characteristics.

It is also an object of this invention to provide a target-selective oil-in-water emulsion that is shelf stable and heat stable so that it can be heat sterilized.

It is a further object of this invention to provide a method of preparing a target-selective oil-in-water emulsion which is chylomicron remnant-like, shelf and heat stable, and substantially free of liposome contamination.

SUMMARY OF THE INVENTION

The foregoing and other objects are achieved improved lipophilic which is a new and improved lipophilic radiopaque agent suitable for incorporation into synthetic oil-in water lipid emulsions. More particularly the compou low molecular weight lipophilic aromatic acid-derived polyhalogenated compounds of a size that, when formulated as an oil-in-water emulsion, does not migrate through the vascular walls as water soluble, low molecular weight agents do. Preferably the molecular weight of the contrast agents of this invention is from about 500 to about 1500.

The novel compounds of this invention preferably have a chemical structure represented by the formula:

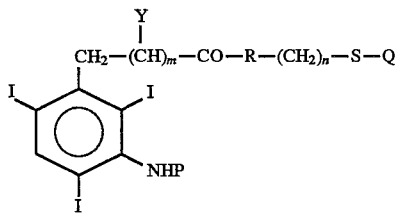

Formula I wherein Y is selected from the group consisting of hydrogen, ethyl, and methyl substituents and m is an integer from zero to 6;

R is selected from the group consisting of —O—, —NH—, and —NCH$_3$—;

P is selected from the group consisting of hydrogen and acyl or fatty acid moieties with up to three double bonds and containing from 2 to about 26 carbons;

S is —O—, —NH—, or —NCH$_3$—; and Q is an aliphatic acid moiety with up to three double bonds and containing from 10 to about 26 carbons; and and wherein n is an integer from 2 to 6. It is preferred that at least one of R and S is —O—.

DESCRIPTION OF THE PREFERRED EMBODIMENT

Figure 1:
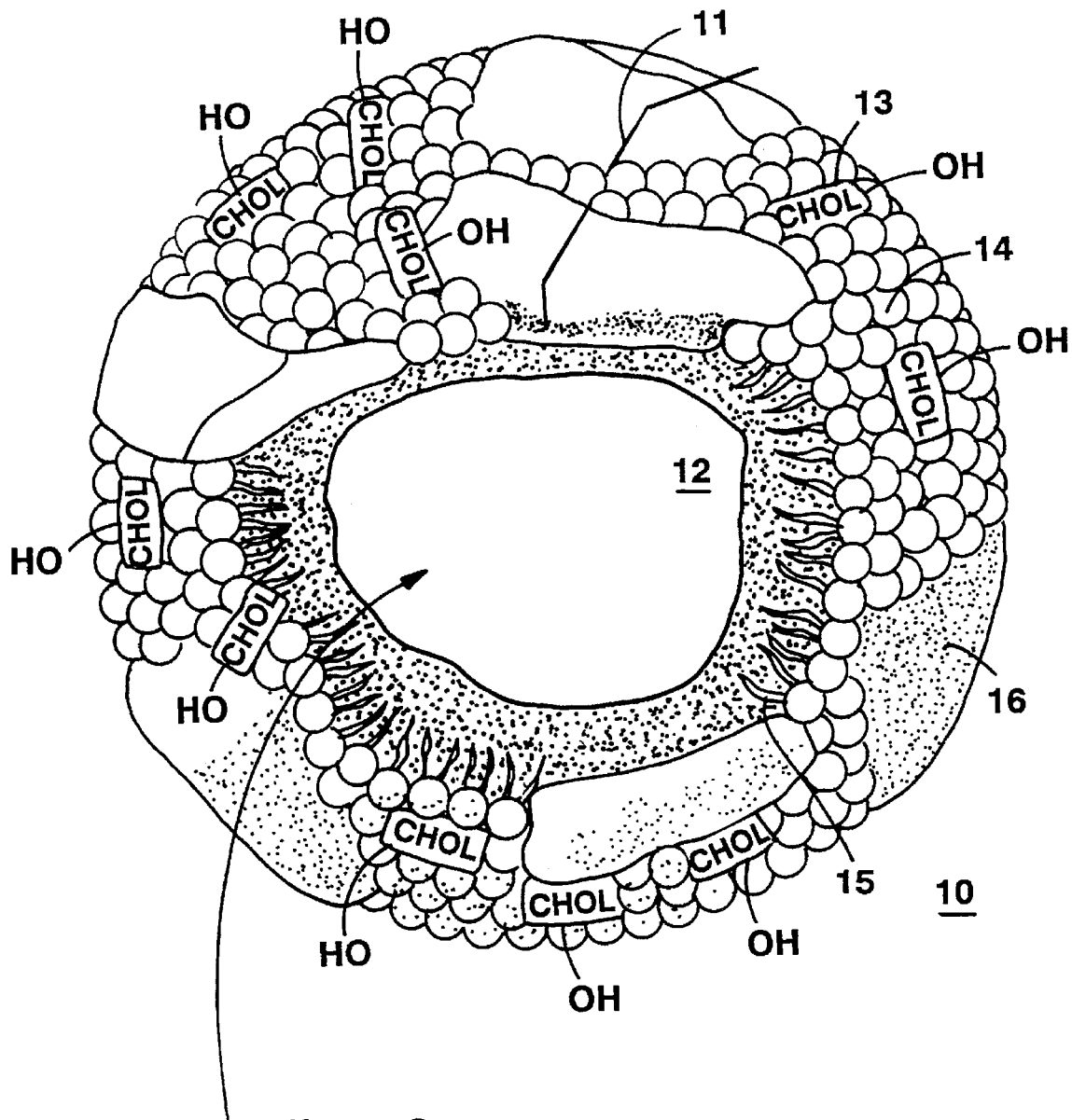
FIG. 1 is a diagram of an oil phase particle of an oil-in-water emulsion of the present invention.

The novel contrast agent compounds provided by this invention are characterized as low molecular weight lipophilic polyhalogenated aromatic acid-derived compounds of a size that, when formulated as an emulsion, do not migrate through the vascular walls as water soluble, low molecular weight agents do.

As used herein the term "aromatic acid" includes all carboxylic acids which contain one aryl group and at least one carboxylic group. For instance, included within "aromatic acids" are benzoic acid and aryl alkanoic acids, which can be either linear or branched.

In one embodiment, the chemical structure of the novel contrast agent compounds provided by this invention is tripartite, being composed of three moieties: an aromatic acid-derived moiety; an aliphatic linker derived fore a bifunctional aliphatic moiety; and an oil soluble (lipophilic) moiety derived from a saturated or unsaturated fatty acid. Preferbly, the molecular weight of the contrast agents of this invention is from about 500 to about 1500.

The aromatic acid-derived compounds of the invention are either oily or are oil soluble, for instance in triolein and/or soy-bean oil.

More particularly, in this embodiment the novel contrast agents have the chemical structure represented by Formula I below:

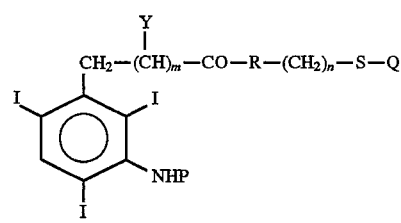

Formula I wherein Y is selected from the group consisting of hydrogen, ethyl, and methyl substitutents and m is an integer from zero to six;

R is selected from the group consisting of —O—, —NH—, and —NCH$_3$—;

P is selected from the group consisting of hydrogen and acyl or fatty acid moieties with up to three double bonds and containing from 2 to about 26 carbons;

S is —O—, —NH—or —NCH$_3$—; and Q is a saturated or unsaturated fatty acid moiety with up to three double bonds containing from about 10 to 26 carbons, and wherein n is an integer from 2 to 6. Preferably, at least one of R and S is —O—.

It is further preferred that Q be derived from an oil soluble acid, such as a saturated or cis unsaturated fatty acid moiety containing from about 10 to 26 carbons; most preferably oleic, linoleic or linolenic acid.

The most preferred compounds for the practice of this invention are Compound Ib and Compound IIIb.

Alternatively the contrast agent compounds are bipartite in structure and lack the bifunctional linker of the compounds of Formula I. These bipartite compounds have a chemical structure represented by Formula II below:

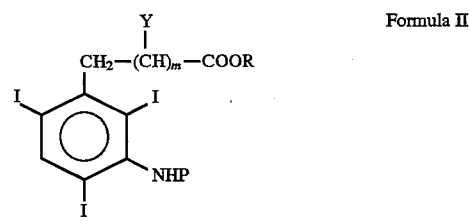

Formula II wherein Y is selected from the group consisting of hydrogen, ethyl, and methyl substitutents and m is an integer from zero to six;

P is selected from the group consisting of hydrogen, an acyl or fatty acid moiety with up to three double bonds and containing from 10 to about 26 carbons; and wherein R is a saturated or unsaturated alkyl moiety with up to three double bonds containing from 10 to about 26 carbons.

Specific examples of the compounds of his invention include, but are not limited to:

| | |
|---|---|
| Compound Ib | {N-methyl-N-(2-hydroxyethyl)-iopanamide} oleate |
| Compound IIb | {N-methyl-N-[2-(methylamino)-ethyl] iopanamide} oleamide |
| Compound IIIb | [3-hydroxypropyl iopanoate] oleate |

Figure 2:
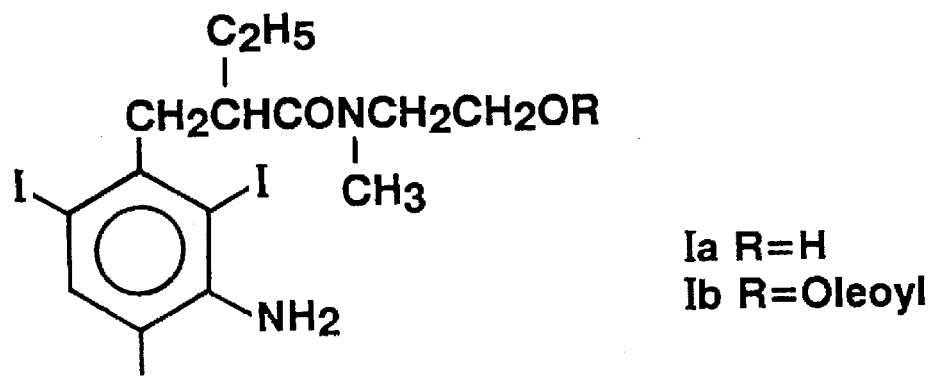
FIG. 2 is a chart showing the chemical structure of compounds of the invention.
Figure 2:
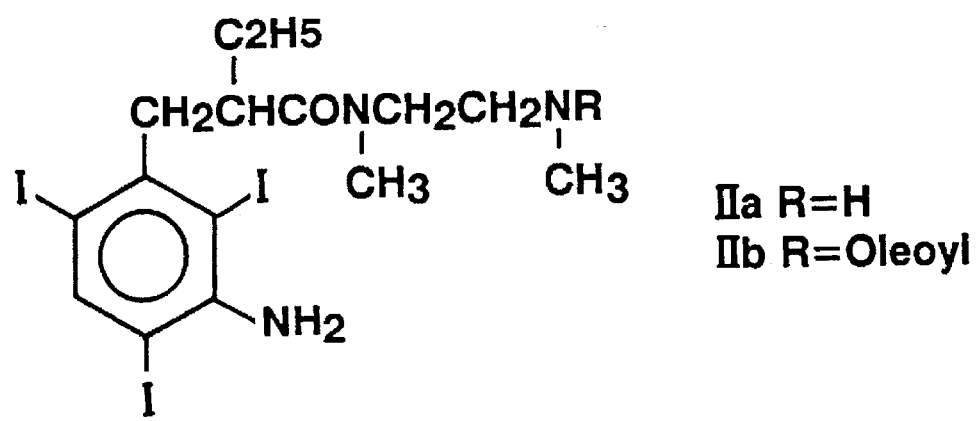
Figure 2:
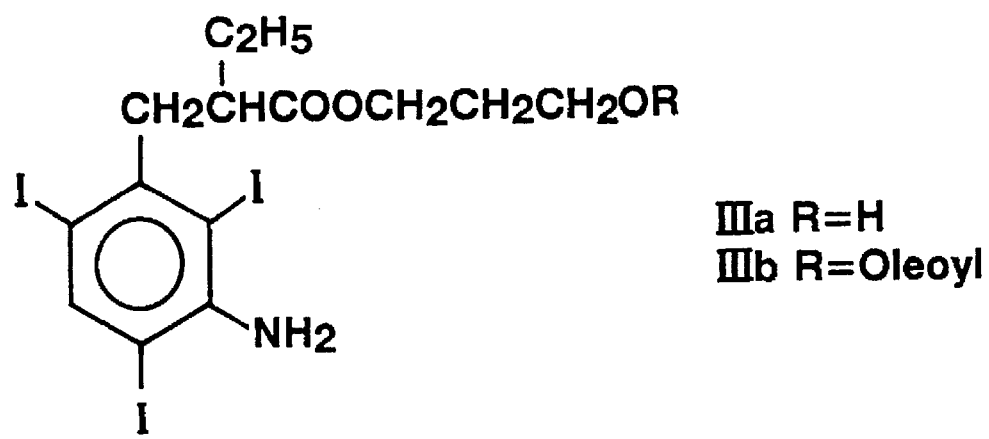

The chemical structures of these compounds are shown in FIG. 2.

The tripartite compounds are synthesized by utilizing the bifunctional linker moiety to link together the two acids into a stable ester or amide compound, using techniques well known in the art. Iopanoic acid is preferred because it is commercially available and has a proven safety record. The term "aromatic acid derived" as used herein encompasses synthesis of the esters or amides from iopanoic acid (3-amino-2,4,6-benzene-α-ethylpropanoic acid), as well as from 2,4,6-triiodo benzoic acid. Examples of synthetic technique are illustrated in Example 1 below. The starting materials can be purchased off the shelf, no heat is needed to drive the reaction, and it can be performed in a single reaction vessel.

If the oil soluble saturated or cis unsaturated fatty acid moiety contains at least 10 carbons, the product compound becomes oil soluble.

FIG. 1 is a diagram of an oil phase particle 10 of the present invention. A lipophilic lipid core 12 is surrounded by a monolayer 11 consisting of an emulsifier and cholesterol 13. The lipid core contains a pharmacologically inert fat or oil, such as a triglyceride, for example triolein) and the polyiodinated aromatic acid-derived compound of the invention. The polar moieties (spheres 14, e.g., polar head portions of a phospholipid emulsifier) of the monolayer face outward into the bulk water phase (not specifically shown); whereas the nonpolar moieties (tails 15) of the monolayer are oriented toward the lipid core. A purely lipophilic compound to be delivered in accordance with the principles of the invention would reside entirely in the core of the lipid particle beneath the monolayer. The lipophilic tail may intermix with the lipophilic tails of the phospholipid/cholesterol components of the monolayer or may extend into the core. FIG. 1 also shows large amorphous structures 16 which represent apolipoproteins.

The oil-in-water emulsions of this invention resemble endogenous lipoproteins in order to take advantage of the natural lipid transport system of a living being and, when they contain the lipophilic radiopaque agents of the present invention are useful as a target-selective delivery vehicle. In specific embodiments, the oil-in-water emulsion simulates chylomicron remnants so that the lipophilic radiopaque compounds inserted into the lipid core of the emulsion are delivered selectively to the hepatocytes via a receptor-mediated pathway. As used herein, the term "receptor mediated" means that metabolism of the oil-in-water emulsions of the present invention mimics the uptake and clearance of natural chylomicron remnants.

Therefore, the synthetic oil-in-water emulsion containing the lipophilic contrast agents of the present invention is designed to associate with plasma apoproteins such as Apo B and Apo E so as to be "hepatocyte-selective" in comparison to "hepatocyte-specific" emulsions as that term is used in the prior art, without definition.

Figure 3:
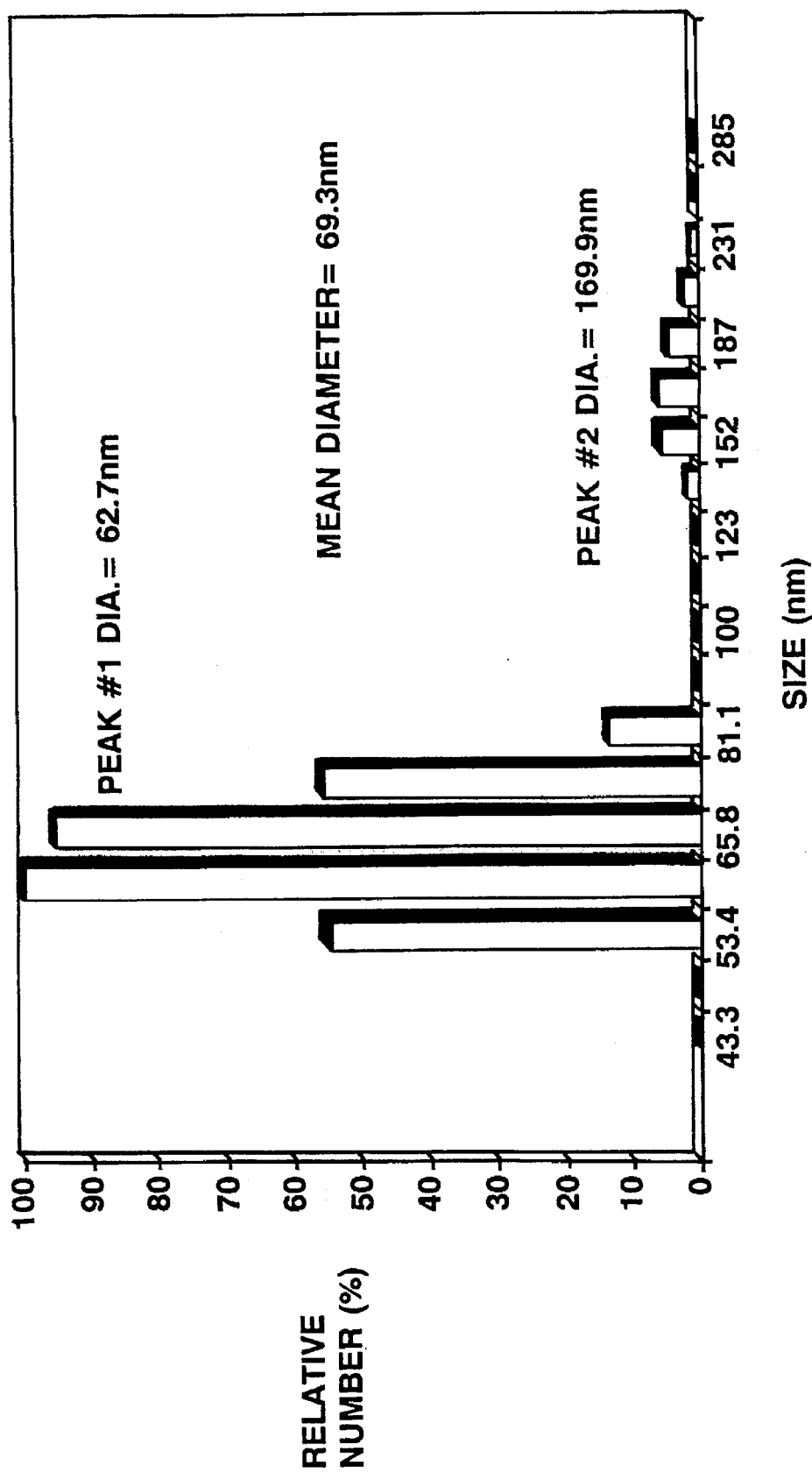
FIG. 3 is a graph showing a representative distribution of the particle size in an emulsion of the present invention (Nicomp Number Weighting analysis).
Figure 4:
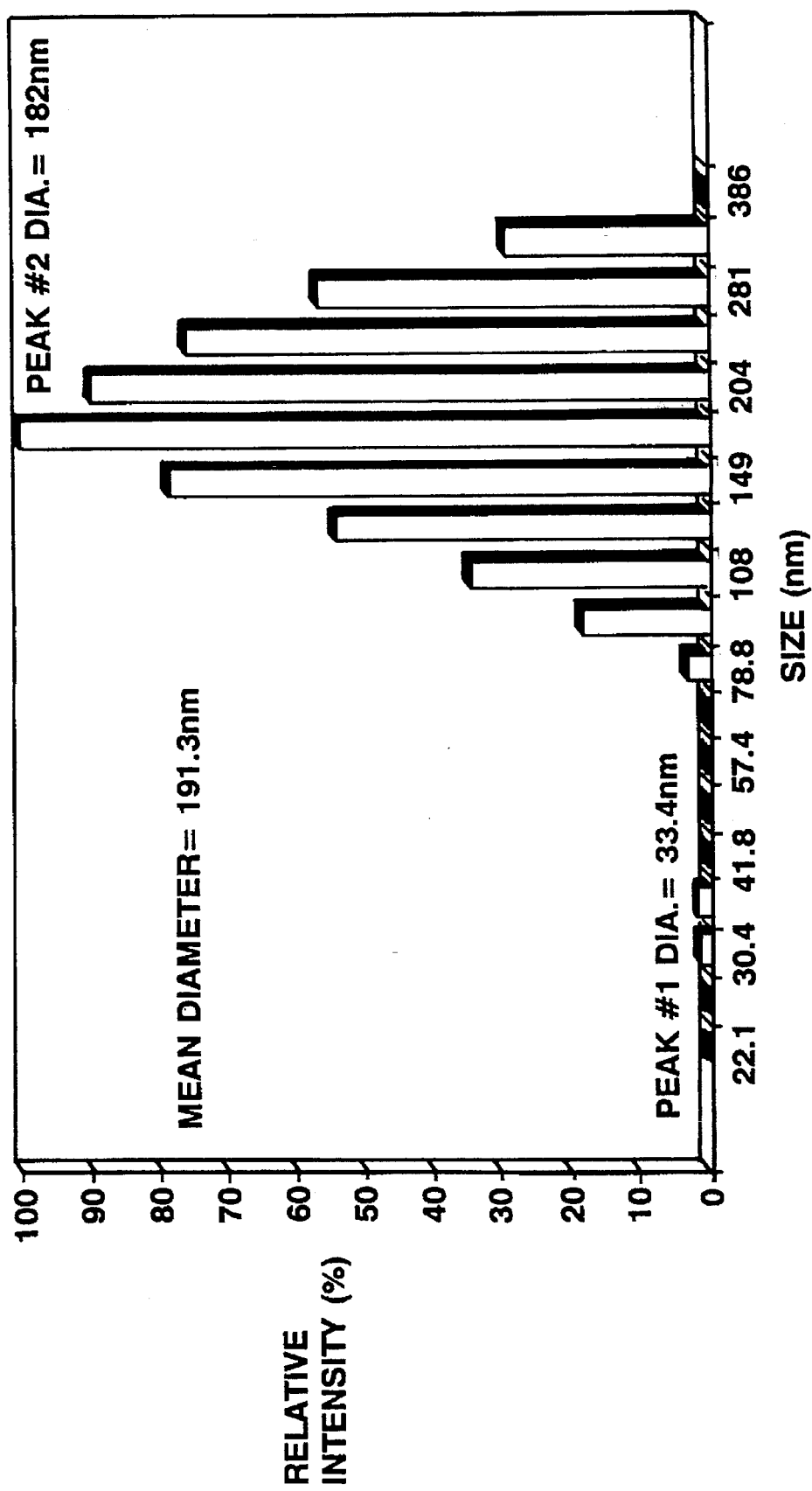
FIG. 4 is a graph showing a representative distribution of the particle size in an emulsion of the present invention (Nicomp Intensity Weighting analysis).

In order to achieve Apo E association, however, the oil phase particles must have the correct size and composition, and must retain the correct size after sterilization and/or over the period of its shelf life. In accordance with the present invention, the main oil phase particle size is between 50 and 200 nm (number weighted), with a narrow size distribution (50 to 300 nm) wherein no more than 2% of the particles have a diameter that falls outside of the range (i.e., being greater than 300 nm). The emulsion should have no detectable particles with a diameter greater than 1 µm. Moreover, the emulsion should not be contaminated with liposomes. Representative distributions of the particle size in an emulsion of the present invention are shown graphically in FIG. 3 (Nicomp Number Weighting analysis) and FIG. 4 (Nicomp Intensity Weighting analysis). The data are presented in both Nicomp Intensity and Nicomp Number weighted formats to enable determination of not only the diameter at which most of the particles exist (number weighting), but also the presence of small, but significant populations of large particles (intensity weighting). The distribution should not have any particles greater than 1 µm. Nor should the emulsion contain more than a minimal amount of liposomes.

In addition, the composition must contain a sterol, which is preferably cholesterol, in an amount of up to 5% by weight in order to stabilize the emulsion and facilitate its association with Apo E, and preferably in the range of 0.4 to 0.5% (w/v) for hepatocyte-selective delivery of iodinated embodiments of the lipophilic agents of the invention. In accordance with preferred embodiments of the invention, the molar ratio of cholesterol to emulsifier, which may be a natural, synthetic, or semi-synthetic phospholipid, has been found to directly affect the particle diameter and dimensional stability. The preferred molar ratio of cholesterol to phospholipid for achieving an emulsion which successfully mimics chylomicron remnants is in thee range of 0.05 to 0.70, and more specifically at about 0.40 for hepatocyte-selective delivery of iodinated compounds. "Hepatocyte-selectivity" as the term is used herein can be demonstrated by a liver to spleen uptake ratio of >4:1 at 30 minutes after injection based on % dose/organ values and biliary clearance and elimination profiles. Based on the entire body of scientific literature describing the anatomical features of the hepatocytes and the surrounding sinusoidal spaces, particles with a diameter greater than approximately 300 nm are unable to access the surface of the hepatocytes. A hepatocyte-selective vehicle primarily delivers the compounds of the invention intracellularly to the. targeted tissue and does not significantly deliver compound nonspecifically to the surface of the cells (extracellular) or to the sinusoids between the cells.

As a composition, the synthetic heat stable hepatocyte-selective oil-in-water emulsion of the present invention has the general formula:
1. up to 50% (w/v) lipophilic core components;
2. up to 10% emulsifier (w/v);
3. up to 5% cholesterol (w/v);
4. up to 5% osmolarity adjusting agent (w/v);
5. optionally, up to 5% antioxidant (w/v); and
6. sterile, distilled water to final volume.

The types of agents that can be delivered to the hepatocytes by incorporation into the lipophilic core of the synthetic oil-in-water emulsions of the present invention are lipophilic compounds, which may be bioactive or bioinactive. The lipophilic core components comprise up to 50% (w/v) of the emulsion, and preferably between about 10% and 30% (w/v). The lipophilic core may comprise any pharmaceutically acceptable fat or oil of natural, synthetic, or semi-synthetic origin that is a pharmacologically inert nonpolar lipid and will locate in the lipophilic core of the oil-h-water emulsion. Specific examples include, without limitation, triglycerides, illustratively, triolein, a naturally-occurring triglyceride of high purity, or oils of animal or vegetable origin, such as soybean oil, safflower oil, cottonseed oil, fish oils, and the like.

In a preferred embodiment, the lipophilic core includes the radiopaque lipophilic aromatic acid-derived compounds of the invention, which may be used for diagnostic or therapeutic purposes. For diagnostic purposes, exemplary agents include, but are not limited to, iodinated or fluorinated compounds, which may contain a stable or radioactive isotope of the halogen.

In particularly preferred embodiments, the lipophilic core includes a mixture of at least one pharmacologically inert oil and a bioactive or inactive agent in a molar ratio in the range of 0.3 to 2, and more preferably 1:1. Preferably, the lipophilicity of each core component is comparable to ensure suitable blending of the lipid components.

In iodinated embodiments, polyiodinated aromatic acid derivatives, such as iopanoic acid, can preferably be used. Clinically, $^{122}$I, $^{123}$I, $^{125}$I, and $^{131}$I are the iodine isotopes most often used with currently available scanning instrumentation. Of course, $^{131}$I-radiolabeled aromatic acid amides or esters may be used for therapeutic purposes, as is known in the art. However, any radioactive isotope of iodine is within the contemplation of the invention. A listing of all iodine isotopes is available at pages B-303–B-305 of the *Handbook of Chemistry and Physics*, 38th edition, CRC Press, 1977–1978. It should be noted that $^{127}$I is the naturally-occurring stable isotope and is not considered to be "radioactive".

In fluorinated embodiments, the compounds of the invention are derived from stable ($^{19}$F) fluorinated lipophilic aromatic acids and can have the chemical structure represented by the formula:

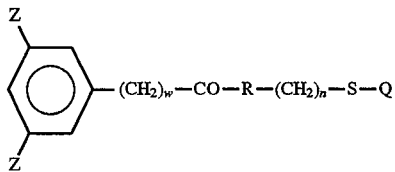

Formula III wherein Z is either —CF$_3$ or —CH$_2$C(CF$_3$)$_3$ and w is an integer from zero to 10;

R is selected from the group consisting of —O—, —NH—, and —NCH$_3$—;

S is —O—, —NH—, or —NCH$_3$—; and Q is an aliphatic acid moiety with up to three double bonds containing from about 10 to 26 carbons; and wherein n is an integer from 2 to 6. Preferably, at least one of R and S is —O—.

Alternative fluorinated compounds will have the chemical structure represented by the formula:

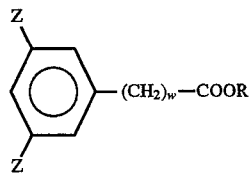

Formula IV wherein Z is either —CF$_3$ or —CH$_2$C(CF$_3$)$_3$ and w is an integer from zero to 10;

wherein R is a saturated or unsaturated alkyl moiety with up to three double bonds containing from about 10 to 26 carbons.

Specific examples illustratively are 3,5-bis (trifluoromethyl)-benzoic acid and 3,5-bis (perfluoro-1H, 1H-neopentyl)-benzene heptanoic acid. The latter compound is described in full in U.S. Pat. No. 5,401,493, which is incorporated herein in its entirety. Of course, these examples are merely illustrative of the many specific examples of lipophilic fluorinated aromatic acid compounds suitable for use in the practice of the invention, and are not in any way intended to be exclusive or limiting.

In addition to the polyhalogenated aromatic acid-derived compounds of this invention, therapeutic agents can be included in the lipophilic core of the synthetic oil-in-water emulsion of the present invention. Such therapeutic agents may include lipophilic derivatives of oligonucleotides or nucleic acids, or lipophilic derivatives of anti-cancer agents, such as esters of methotrexate, mitomycin C, fluorodeoxyuridine or doxorubicin.

The monolayer surrounding the nonpolar lipophilic core comprises up to about 10% (w/v) of a polar lipid monolayer component, which may be an emulsifier. Phospholipids of natural, synthetic, or semi-synthetic origin are suitable for use in the practice of the invention. Traditional lipid emulsions for delivery of bioactive agents use natural phospholipids, such as soy lecithin and egg phosphatidylcholine (e.g., Intralipid). The emulsion components may comprise synthetic, semi-synthetic, and/or naturally occurring components of known origin, purity and relative concentrations. However, the lipid components of the invention are generally selected so that the polyhalogenated aromatic compounds of the invention, most particularly the saturated or unsaturated fatty acid moiety of the contrast agent is soluble therein. For example, use of lecithin and/or triolein is particularly preferred when the Q moiety of Structure I compounds is derived from oleic acid. One skilled in the art will be able to select the appropriate lipids for use with any given polyhalogenated aromatic acid-derived compound of this invention. However, the improper use of egg lecithins (mixtures of phospholipids) and/or crude oils (cottonseed poppy seed, and the like) in prior art emulsions is to be, avoided, and may result in variable and non-reproducible compositions.

In a specific advantageous embodiment, dioleoylphosphatidylcholine (DOPC) is used as an emulsifier, or monolayer surfactant. DOPC is a semi-synthetic, chemically defined phospholipid emulsifier of high purity (available from Avanti Polar Lipids, Alabaster, Aa). Of course, other surface active agents which are suitable for parenteral use can be substituted for all or a portion of the polar lipid monolayer component. The naturally-occurring phospholipids are advantageous; because these phospholipids have a reasonable potential for interaction with. apolipoproteins and an appropriate transition temperature, i.e., they are in the liquid. state at physiologic temperatures.

The osmolality of the emulsion is adjusted to 400–500 mOsm/kg with up to 5% w/v of an osmolality adjusting agent, such as USP glycerol or glucose. The oil-in-water emulsion of the present invention produces a delivery vehicle which is nearly isotonic relative to blood. This is in sharp contrast to most commonly used ionic contrast media which have osmolalities 3 to 5 times higher than that of the blood and can result in pain and tissue injury at the site of injection.

The remainder of the emulsion formulation comprises the bulk or aqueous phase. In the practice of a preferred embodiment of the present invention, the aqueous phase is sterile water of a grade suitable for parenteral administration. The inclusion of salt (NaCl) in the aqueous phase, such as by the use of 0.9% saline, results in emulsions which have a mean particle diameter as much as twice the size of salt-free emulsions. Furthermore, the presence of salt in the formulation has an adverse effect on the ability of the emulsion to survive autoclave sterilization without a significant change in mean particle size as well as on the temporal stability of an autoclaved emulsion.

In addition to NaCl, pH-adjusting agents frequently used in the formulation of parenteral emulsions, such as NaOH or the sodium salts of most aqueous buffers, introduce excessive sodium ions into the bulk phase. These agents have been found, to have deleterious effects on particle size, stability, and the ability to survive autoclaving.

Other conventional additives, such as antioxidants, buffers, preservatives, viscosity adjusting agents, and the like, may be included in the composition. In particular up to 5% w/v of an antioxidant, such as α-tocopherol, flavinoids, BHT, or BHA, is recommended. However, the additive should not adversely affect the physical characteristics of the emulsion, such as particle size, or shelf and heat stability.

The techniques used to formulate the oil-in-water emulsions of the present invention are important in achieving small particle diameter, uniform size distribution, lack of liposome contamination, etc. all of which contribute to hepatocyte-selectivity and heat stability.

A method for making the oil-in-water emulsions containing the polyhalogenated aromatic acid-derived compounds of the invention is also provided. The lipophilic components of the oil-in-water emulsion including nonpolar core lipids, polar lipid emulsifiers, and other lipophilic components, such as bioactive or bioinactive agents, are blended together to form a preblended lipid phase. The aqueous components are combined and added to the preblended lipid phase. The preblended. lipid phase and aqueous components are homogenized to form a crude oil-in-water emulsion. The crude oil-in-water emulsion is then subjected to ultra high energy emulsification to produce a fine oil-in-water emulsion having a mean particle diameter of the oil phase between 50 to 200 nm with greater than 98% of the particles being less than 300 nm. In preferred embodiments of the invention, the fine oil-in-water emulsion is sequentially filtered.

In a preferred method for making the oil-in-water emulsions of the invention, the lipid components are initially blended or homogenized using a high speed mixer, such as a Polytron homogenizer (Kinematica GmbH, Lucerne, Switzerland), or blender (Silverson Machines, Inc.). operating at 10,000 rpm at 55° C. for at least 5 minutes. Then, the aqueous components are added to the preblended lipid. components and pre-emulsified by high speed mixing under the same, or similar, conditions to form a crude emulsion. Final processing is accomplished with ultra high energy mixing equipment, such as a MicroFluidizer high pressure homogenizer (Model 110Y, Microfluidics Corp., Newton, Mass.; see, U.S. Pat. No. 4,533,254), or equivalent equipment, operating in the recycling mode at 30°–60° C. and 10,000 to 30,000 psi, and preferably at about 12,500–18,200 psi, for up to about 20 minutes. After processing, the emulsion is passed sequentially through 0.45 μm and 0.22 μm sterile filters to remove any large particles and partially sterilize the product.

The temperature for high energy mixing is illustrative, and should be chosen. relative to the bioactive agent. In other words, the temperature should be greater than or equal to the transition temperature or melting point of the bioactive agent: or contrast agent. An upper bound however, is determined by whether the temperature would cause degradation or decomposition of any components in the composition.

The use of an ultra high pressure homogenizer ensures small particle size with a narrow size range distribution so that the resulting emulsion will simulate chylomicron remnants. Conventional systems for forming emulsions, such as homogenizers, sonicators, mills, and shaking systems provide a shearing force on the liquid components; whereas the ultra high energy mixing equipment puts the emulsion components under pressure and forces them through small openings to reduce particle size. Size distribution may be measured by a Nicomp 370 Dynamic Laser Light Scattering Autocorrelator (Nicomp Particle Sizing Systems, Santa Barbara, Calif.) or similar equipment. A lipid emulsion, which is suitable for the practice of the present invention, will have a mean particle diameter less than about 300 nm, and preferably the range of 50 to 200 nm as measured by Nicomp number weighting analysis. The particles should have a narrow size distribution, with about 98% of the particles being in the 50 to 300 nm. No particles should be detected with a diameter of greater than 1 μm.

The size distribution should be stable for a minimum shelf-life period of ninety days. By "shelf-stable" is meant that the mean diameter of the emulsion particles should not change by greater than 15% at 90 days post-formulation, or more than 20% over the shelf-life. The emulsion can be stored for up to 2 years at room temperature. Under ideal conditions, the product is stored under nitrogen at 4° to 8° C. and is, preferably, protected from light.

In preferred embodiments, the emulsion is sterilizable, for example by heat or cold filtration. Standard or intermittent autoclaving techniques, such as 20 minutes exposure to pressurized steam at 121° C., should not adversely affect the size distribution of the emulsion. As used herein, the term "heat stable" means that the emulsion has the ability to withstand standard heat sterilization (e.g., 20 minutes exposure to steam at 121° C.) without a significant change in the mean particle size distribution. A significant feature of the composition/formulation process of the present invention is the ability of the emulsion to retain its ability to associate Apo E following autoclaving. Therefore, the term "heat stable" as used herein to define the microemulsion of the present invention includes the ability to associate with Apo E after heat sterilization.

The present invention additionally presents a method of using the polyhalogenated aromatic compounds as diagnostic and/or therapeutic agents. In one embodiment, an oil-in-water emulsion of the present invention containing a polyhalogenated aromatic acid ester or amide is administered to a mammal, and the mammal is subjected to x-ray or computer tomographic imaging after the emulsion has reached the target site. In alternative methods of use, appropriate oil-in-water emulsions, containing embodiments of the compounds of the invention suitable for other diagnostic modalities, such as $^{19}$F-MRI, may be administered for visualization and/or detection. For instance, non-proton magnetic resonance imaging of the liver has been accomplished in the prior art with emulsified perfluorocarbons, such as Fluosol and perfluoroctylbromide, which are sequestered not only by hepatic Kupffer cells, but also by reticuloendothelial cells of the spleen and bone marrow. However, the polyfluorinated aromatic acid-derived contrast agents of the invention can also be incorporated into chylomicron-like microemulsions useful as magnetic resonance contrast agents.

In still another method of use embodiment, a therapeutic agent, such as a $^{131}$I-containing aromatic acid-derived compound is delivered to a target site in an oil-in-water emulsion of the present invention to treat a disease state located at the target site. For example a $^{131}$I-aromatic acid-derived compound is delivered to a target site located in the liver using a hepatocyte-specific embodiment of the oil-in-water emulsion of the invention.

The hepatocyte-selective nature of the emulsions of the present invention permits imaging of the hepatobiliary system. Therefore, use of the emulsions would be particularly advantageous in the diagnosis and/or treatment of any disease that alters the hepatic lipase and lysomal acid lipase activity, such as diabetes, cancer, cirrhosis, alcoholism, primary and metastatic liver tumors, hepatitis, cholecystitis, obstructive jaundice, liver transplant functional assessment, fibrotic liver, fatty liver, and many others.

In an alternative embodiment, the aliphatic acyl or alkyl moiety of the aromatic acid-derived compound contains at least 10 carbons, and preferably is a cis unsaturated fatty acid or alkyl moiety, so that the polyhalogenated aromatic acid ester can be made oily rather than merely lipophilic. Such oily embodiments of the compounds can be used for imaging and therapeutic purposes without being incorporated into an oily carrier, and provide the additional benefit that the radioisotope administered to the patient in a given volume of emulsion administered is greatly concentrated.

The following examples illustrate the manner in which the invention can be practiced. It is understood, however, that the examples are for the purpose of illustration and the invention is not to be regarded as limited to any of the specific materials or conditions therein.

EXAMPLE 1

In the following, 3-Amino-α-ethyl-2,4,6-triiodobenzenepropionamide will be called "iopanamide."

1. Preparation of N-methyl-N-(2-hydroxyethyl)-iopanamide (Ia).

A solution of iopanoic acid (9.9 g, 17 mmole) and 1-hydroxybenzotriazole (2.5 g, 18.5 mmole) in dry pyridine (100 ml) was evaporated in vacuo until about 20 ml of anhydrous residue was left. Subsequently, 1,3-dicyclohexylcarbodiimide (DCC; 3.8 g, 18.5 mmole) in dry dichloromethane (50 ml) was added. After stirring for 4 hours, 2-(methylamino)-ethanol (3.8 g, 18.5 mmole) in dichloromethane (100 ml) was added and the stirring continued overnight. The precipitate was then filtered off, and the filtrate evaporated in vacuo until the residue was free of pyridine. The product was then dissolved in chloroform and extracted with aqueous $NaH_2PO_4$. The organic layer was dried with $MgSO_4$ and evaporated. The residue was dissolved in a minimal amount of chloroform and added dropwise to cyclohexane with stirring. The semi-solid precipitate was collected, dissolved again in chloroform and finally isolated by evaporation of the solvent in vacuo, in 95% yield. This procedure yielded a compound with the following parameters: $^1$H NMR ($CDCl_3$); 8.10 (s, 1H, aromatic), 4.90 (br, s, 2H, $NH_2$), 3.80 (m, 2H, $CH_2$), 3.32 (m, 4H, 2 $CH_2$), 3.15 (m, 1H, CH), 2.90 (s, 3H, $NCH_3$), 1.40–2.10 (m, 2H, $CH_2$ and 0.90 (t, 3H, $CH_3$).

2. Preparation of the oleate of N-methyl-N-(2-hydroxyethyl)-iopanamide (Ib).

To an anhydrous solution containing Ia (8.0 g, 12.7 mmole), p-dimethylaminopyridine (100 mg) and oleic acid (4.0 g, 14.2 mmole) in dichloromethane (75 ml) was added DCC (3.05 g, 14.8 mmole). After 20 hours of stirring the mixture was filtered. The filtrate was repeatedly extracted with aqueous NaCl and subsequently dried with $MgSO_4$. The solvent was removed and the residue chromatographed on a silica gel column with ethylacetatehexane (1:3 v/v) as solvent. Compound Ib was isolated as a faintly yellow oil in 88% yield (10 g) HPLC (Alltima C18, 5µ, Alltech; 25% tetrahydrofuran, 5% water, 0.1% trifluoroacetic acid in methanol) showed the compound had a purity of 99.4%.

Elemental analysis (calculated for $C_{32}H_{51}I_3N_2O_3$): C, 43.64% (43.06); H, 5.59% (5.72); N, 3.26% (3.14). $^1$H NMR ($CDCl_3$): 8.40 (s, 1H, aromatic), 5.30 (t, 2H, CH=CH), 4.75 (br, 2H, $NH_2$), 4.2–3.9 (m, 6H, 3 $CH_2$), 3.15 (m, 1H, CH), 2.85 (s, 3H, $NCH_3$), 2.30 (m, 2H, $CH_2$), 1.95 (m, 2H, $CH_2$), 1.65 (m, 4H, $2CH_2$), 1.25–1.27 (m, 24H, 12 $CH_2$) and 0.83–0.86 (t, 6H, $2CH_3$).

3. Preparation of N-methyl-N-[2-(methylamino)-ethyl]-iopanamide (IIa).

A solution of iopanoic acid (13.5 g, 23.6 mmole) and 1-hydroxybenzotriazole (3.63 g, 26.9 mmole) in anhydrous pyridine (50 ml) was evaporated to near dryness under reduced pressure and exclusion of moisture. 1,3-dicyclohexylcarbodiimide (DCC, 6.3 g, 30.5 mmole) was dissolved in anhydrous dichloromethane (100 ml) and added to the pyridine containing residue. The mixture was stirred for 3 hours before N,N'-dimethylethylenediamine (6.2 g, 70.3 mmole) was added and then left stirring overnight. The precipitate of 1,3-dicyelohexylurea was filtered off and washed with dichloromethane. The combined filtrate was evaporated in vacuo, giving an oily residue. TLC ($SiO_2$, 20% methanol/chloroform) showed the formation of essentially one UV absorbing spot. The residual oil was left under vacuum (0.05 mm Hg) overnight. The oil was purified on a silica gel column with 15% methanol in chloroform, giving a glassy oil in 74% yield.

$^1$H NMR ($CDCl_3$): 8.08 (s, 1H, aromatic), 4.86 (broad s, 2H, $NH_2$), 3.5–3.9; (m, 2H, $CH_2$), 3.2–3.4 (t, 2H, $NCH_2$—), 3.15 (m, 1H, CH), 2.9–3.2 (t, 2H, $NCH_2$—), 2.83 (s, 3H, $NCH_3$), 2.64 (s, 3H, $NCH_3$), 1.81–1.95 (m, 2H, $CH_2$) and 0.82 (t, 3H, $CH_3$).

4. Preparation of the oleanmide of N-methyl-N-[2-(methylamino)-ethyl]-iopanantide (IIb).

A solution of oleic acid (5.32 g, 18.0 mmole) and 1-hydroxybenzotriazole (2.8 g, 20 mmole) in pyridine (60 ml) was concentrated in vacuo to reduce the volume by 50%. DCC (4.2 g, 20 mmole) was dissolved in dry dichloromethane (150 ml) and added to the anhydrous pyridine mixture with stirring. 1,3-dicyclohexylurea started to precipitate immediately. After 2 hours, the mixture was added to an anhydrous solution of compound IIa (11.0 g, 17.2 mmole) in pyridine (50 ml). The mixture was stirred overnight and then extracted exhaustively with aqueous $NaH_2PO_4$. The organic layer was dried with $MgSO_4$ and evaporated to dryness. The residue was chromatographed on silica gel with chloroform. After being kept overnight in a vacuum (0.05 mmHg), it was obtained as a faintly yellow oil in 77% yield (11.8 g). HPLC (Supelcosil LC 18-DB, 5 µm; 75% acetonitrile, 20% tetrahydrofuran, 5% water) showed the compound was more than 99% pure.

Elemental analysis (calculated for $C_{33}H_{54}I_3N_3O_2$): C, 44.52% (43.76); H, 6.11% (5.97); N, 4.71% (4.65). $^1$H NMR ($CDCl_3$):8.08(s, 1H, aromatic), 5.35 (t, 2H, CH=CH), 4.75 (broad s, 2H, $NH_2$), 3.5–3.8 (m, 2H, $CH_2$), 3.15 (m, 1H, CH), 3.2 –3.4 (m, 2H, $NCH_2$), 2.8–3.2 (m, 2H, $NCH_2$), 2.94 (s, 3H, $NCH_3$), 2.89 (s, 3H, $NCH_3$), 2.2–2.4 (m, 2H, $CH_2$), 1.97–2.0 (m, 4H, $2CH_2$), 1.5–1.7 (m, 2H, $CH_2$), 1.25–1.28 (m, 24H, $12CH_2$) and 0.83–0.87 (t, 3H, $CH_3$).

5. Preparation of 3-hydroxypropyl iopanoate (IIIa) 1,3-dicyclohexylcarbodiimide (1.0 g, 4.85 mmole) was added to an anhydrous solution of iopanoic acid (1.0 g, 1.75 mmole), 1,3-propanediol (0.77 g, 10.1 mmole) and pyridine (1 ml) in acetonitrile (50 ml). The mixture was stirred overnight and then filtered to remove 1,3-dicyclohexylurea. The filtrate was evaporated and the residue kept under vacuum (0.02 mmHg) overnight in order to remove all 1,3-propanediol. The crude reaction product was chromatographed on a silica gel column, using a linear gradient (20–50%) of ethylacetate in hexane. Compound IIIa was isolated from the eluate in about 60% yield.

$^1$H NMR (CDCl$_3$): 8.08 (s, 1H, aromatic), 4.85 (broad s, 2H, NH$_2$), 4.22 (t, 2H, OCH$_2$), 3.54 (t, 2H, OCH$_2$), 2.85 (m, 1H, CH), 1.7–2.2 (m, 4H, 2CH$_2$) and 0.92 (t, 3H, CH$_3$).

6. Preparation of the oleate of 3-hydroxypropyl iopanoate (IIIb).

To an anhydrous solution of IIIa (5.6 g, 8.9 mmole), oleic acid (2.8 g, 9.9 mmole) and dimethylaminopyridine (100 mg) in dichloromethane (165 ml) was added DCC (2.18 g, 10.6 mmole). After stirring for 20 hours, the mixture was filtered. The filtrate was washed with water, then dried with MgSO$_4$ and evaporated. The residue was redissolved in ether and filtered to remove additional dicyclohexylurea. Evaporation of the ether gave an oily residue which was chromatographed on silica gel with 15% ethylacetate in hexane. Compound IIIb was isolated from the eluate as a faintly yellow oil in 84% yield. HPLC (conditions as in Section 4 above) showed the compound was more than 99% pure.

Elemental analysis (calculated for C$_{32}$H$_{50}$I$_3$NO$_4$): C, 42.73% (43.02); H, 5.61% (5.60); N, 1.57% (1.57). $^1$H NMR (CDCl$_3$): 8.15 (s, 1H, aromatic), 5.35 (t, 2H, CH=CH), 4.84 (s, 2H, NH$_2$), 4.05–4.06 (m, 4H, 2 OCH$_2$), 3.2–3.4 (m, 2H, CH$_2$), 1.9–2.09 (m, 3H, CH, CH$_2$), 1.75 (m, 4H, 2CH$_2$), 1.26–1.29 (m, 24H, 12 CH$_2$) and 0.87–0.94 (t, 6H, 2CH$_3$).

Formulation of an Oil-In-Water Emulsion.

Water, 81.5 g, glycerol, 4.96 g and Lipoid S75 (Lipoid KG), 2.485 g were mixed with a high-speed blender (Silverson Machines, Inc, Mass.) to give the aqueous part. The oily part was made up in a separate beaker by mixing N-methyl-N-(2-hydroxyethyl)-iopanamide oleate (compound Ib), 6.044 g, triolein (Sigma), 4.157 g, cholesterol, 0.493 g and α-tocopherol, 0.628 g at 50° to 60° C. The warm oil mixture was gradually added by syringe to the aqueous solution, while blending it at 9,900 RPM. The mixing was continued for 30 minutes, while keeping the temperature below 40° C. The particle size, measured on the Nicomp C370 particle sizer, was 2.4 μm (vol.-weighted). Subsequently, the coarse emulsion was homogenized for 15 minutes using a Microfluidizer (Microfluidics 110-Y at a setting of 18,000 psi and 25° C. The mean particle size of the final emulsion was 126 nm (volume-weighted) with 99% of the particles smaller than 247 nm.

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A compound having a chemical structure represented by the formula:

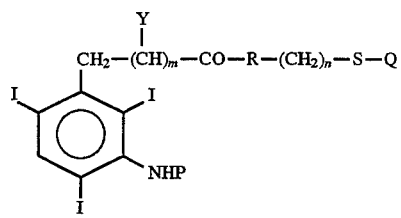

wherein Y is selected from the group consisting of hydrogen, ethyl, and methyl substitutents and m is an integer from zero to 6;

R is selected from the group consisting of —O—, —NH—, and —NCH$_3$—;

P is selected from the group consisting of hydrogen and acyl and fatty acid moieties with up to three double bonds and containing from 2 to about 26 carbons;

S is selected from the group consisting of —O—, —NH—, or —NCH$_3$—; Q is a saturated or unsaturated fatty acid moiety with up to three double bonds and containing from about 10 to 26 carbons; and n is an integer from 2 to 6.

2. The compound of claim 1 wherein at least one of R and S is —O— and Y is ethyl.

3. The compound of claim 2 wherein Y is ethyl, and P is hydrogen.

4. The compound of claim 1 or 3 wherein R is —NCH$_3$—.

5. The compound of claim 1 or 3 wherein S is —NCH$_3$— or —NH—.

6. The compound of claim 1 wherein Q is a cis unsaturated fatty acid.

7. The compound of claim 6 wherein Q is oleic acid.

8. The compound of claim 6 wherein Q is linoleic acid.

9. The compound of claim 6 wherein Q is linolenic acid.

10. The compound of claim 1 wherein at least one of R and S is —O—.

11. The compound of claim 1 wherein Y is hydrogen.

12. The compound of claim 1 having a molecular weight in the range from about 500 to 1500.

13. The compound of claim 2 wherein the iodo substituent is $^{131}$I.

14. The compound of claim 1 wherein the compound is oleamide of N-methyl-N-[2-(methylamino)-ethyl]-iopanamide.

15. The compound of claim 1 wherein the compound is oleate of N-methyl-N-(2-hydroxyethyl)iopanamide.

16. The compound of claim 1 wherein the compound is oleate of 3-hydroxypropyl iopanoate.

17. A compound having a chemical structure represented by the formula:

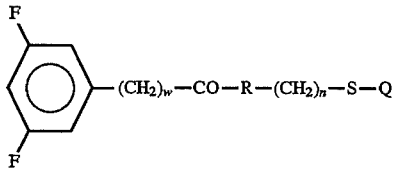

wherein Z is —CF$_3$ or —CH$_2$C(CF$_3$)$_3$ and w is an integer from zero to 10;

R is selected from the group consisting of —O—, —NH—, and —NCH$_3$—;

S is selected from the group consisting of —O—, —NH— or —NCH$_3$—; Q is an aliphatic acid moiety with up to three double bonds containing from about 10 to 26 carbons; and wherein n is an integer from 2 to 6.

18. The compound of claim 17 wherein at least one of R and S is —O—.

19. The compound of claim 17 wherein Z is —CH$_2$C(CF$_3$)$_3$.

20. A compound having a chemical structure represented by the formula:

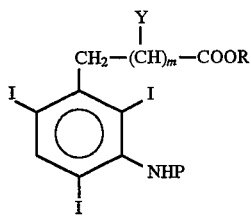

wherein Y is selected from the group consisting of hydrogen, ethyl, and methyl substitutents and m is an integer from zero to 6;

P is selected from the group consisting of hydrogen and acyl and fatty acid moieties with up to three double bonds and containing from 2 to about 26 carbons; and R is a saturated or Unsaturated alkyl moiety with up to three double bonds containing from about 10 to 26 carbons.

21. The compound of claim 20 wherein Y is hydrogen.

22. The compound of claim 20 wherein Y is ethyl and P is hydrogen.

23. The compound of claim 20 wherein P is oleoyl.

24. The compound of claim 20 wherein R is a cis unsaturated alkyl.

25. The compound of claim 24 wherein K is oleyl.

26. The compound of claim 20 wherein Y is hydrogen and P is hydrogen.

27. The compound of claim 20 having a molecular weight in the range from about 500 to 1500.

28. A compound having a chemical structure represented by the formula:

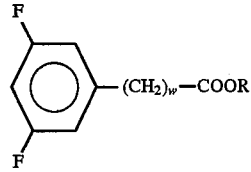

wherein Z is either —CF$_3$ or —CH$_2$C(CF$_3$)$_3$ and w is an integer from zero to 10; and R is a saturated or unsaturated alkyl moiety with up to three double bonds containing from about 10 to 26 carbons.

29. The compound of claim 28 wherein Z is —CH$_2$C(CF$_3$)$_3$ and R contains 18 carbons.

30. The compound of claim 28 wherein Z is —CH$_2$C(CF$_3$)$_3$.

31. A compound having a chemical structure represented by the formula:

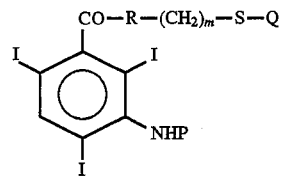

wherein m is an integer from zero to 6;

R is selected from the group consisting of —O—, —NH—, and —NCH$_3$—;

P is selected from the group consisting of hydrogen and acyl and fatty acid moieties with up to three double bonds and containing from 2 to about 26 carbons;

S is selected from the group consisting of —O—, —NH—, or —NCH$_3$—; Q is a saturated or unsaturated fatty acid moiety with up to three double bonds and containing from about 10 to 26 carbons; and n is an integer from 2 to 6.

32. An oil in water emulsion having a lipophilic core surrounded by a monolayer of polar lipids, the emulsion having a mean particle diameter of the oil phase between 50 to 200 nm with greater than 98% of the particles being less than 300 nm, the monolayer including an emulsifier and an amount of cholesterol sufficient to facilitate association with apoprotein E, and the lipophilic core containing at least one compound of claim 1, 17, or 31 and a lipophilic or amphiphilic agent that is pharmaceutically acceptable.

33. The oil in water emulsion of claim 32 wherein the lipophilic agent is triolein.

34. The oil in water emulsion of claim 32 wherein the amphiphilic agent is lecithin.

35. The oil in water emulsion of claim 32 wherein the amount of cholesterol sufficient to facilitate association with apoprotein E is up to about 5% (w/v) of the emulsion.

36. The oil in water emulsion of claim 32 wherein the compound of claim 1 is oleate of N-methyl-N-(2-hydroxyethyl)-iopanamide.

37. An oil in water emulsion having a lipophilic core surrounded by a monolayer of polar lipids, the emulsion having a mean particle diameter of the oil phase between 50 to 200 nm with greater than 98% of the particles being less than 300 nm, the monolayer including an emulsifier and an amount of cholesterol sufficient to facilitate association with apoprotein E, and the lipophilic core contains at least one compound of claim 1, 17, or 31 wherein the compound is oily.

38. A composition of claim 37 wherein the compound has an aliphatic acyl or alkyl moiety having at least 10 carbon atoms.

39. A composition of claim 37 wherein the compound is the oleate of N-methyl-N-(2-hydroxyethyl)-iopanamide.

40. A composition of claim 37 wherein the compound is the oleamide of N-methyl-N-[2-(methylamino)-ethyl]-hydroxyethyl)-iopanamide.

41. A composition of claim 37 wherein the compound is the oleate of 3-hydroxypropyl iopanoate.

* * * * *